United States Patent
Schlaeger (12)

(10) Patent No.: US 6,241,978 B1
(45) Date of Patent: Jun. 5, 2001

(54) METHOD FOR MANUFACTURING, APPARATUS AND TECHNIQUE FOR APPLYING SOLID ANTISEPTIC EMULSIONS OF WAX COMPOSITIONS AND SOLUBLE EXTRACTS OF VEGETATIVE PLANTS TO HAIR

(76) Inventor: Gary D. Schlaeger, 3321 Springfield Rd., Springtown, TX (US) 76082

( * ) Notice: Subject to any disclaimer, the term of this patent is extended or adjusted under 35 U.S.C. 154(b) by 0 days.

(21) Appl. No.: 09/119,143

(22) Filed: Jul. 20, 1998

(51) Int. Cl.$^7$ ................................. A61K 7/06; A61K 7/09
(52) U.S. Cl. ..................... 424/70.2; 424/70.1; 424/401; 424/407; 424/409; 424/417; 424/420
(58) Field of Search ................... 424/70.1, 70.2, 424/401, 407, 409, 417, 420

(56) References Cited

U.S. PATENT DOCUMENTS 4,770,873 * 9/1988 Wolfram et al. ..................... 424/71
5,474,778 * 12/1995 Ichikawa et al. ..................... 424/401

FOREIGN PATENT DOCUMENTS

0283893 * 9/1988 (EP) .

* cited by examiner

*Primary Examiner*—Bennett Celsa
(74) *Attorney, Agent, or Firm*—Arthur F Zobal

(57) ABSTRACT

The cosmetic composition includes hydrophobic lipophilic materials as the principle vehicle carrying the active ingredients in a continuous solid phase, the composition is formed into a hairstick by locating the composition in a container having means to mechanically extrude the composition out of the open end of the container. A unique process is provided for forming the composition and locating the composition in the container. In one embodiment the composition is layered alternately between removably impermeable membranes in the container such that when the top layer of composition is used, the next lower membrane may be removed to allow the next layer of composition to be used.

7 Claims, 4 Drawing Sheets

METHOD FOR MANUFACTURING, APPARATUS AND TECHNIQUE FOR APPLYING SOLID ANTISEPTIC EMULSIONS OF WAX COMPOSITIONS AND SOLUBLE EXTRACTS OF VEGETATIVE PLANTS TO HAIR

BACKGROUND OF THE INVENTION

1. Field of the Invention

The present invention relates to a process for the manufacture of a sanitary color-enhancing hair fixative composition in combination with an apparatus and method for applying the composition to hair in situ.

This invention pertains to the field of cosmetics and to the specific field of haircare. In hairstyling it is desirable to create an expanded "puffed up" or "fluffed up" appearance of increased body and volume of hair by separating individual hair shafts and causing them to protrude outwardly from the skin in an upright position somewhat perpendicular at large acute angles in relation to the skin. It is also frequently common practice in the art of hairstyling and desirable by those skilled in the art to sculpt a slicked-back, flattened appearance in which the hair describes small acute angles in relation to the skin.

To achieve these useful and desirable appearances stylists skilled in the art employ the application of liquid adhesives and chemical "holding agents" involving often complex sequential processes composed of many interrelated sequential consecutive steps to cause individual hair shafts to remain in a desired somewhat upright orientation in relation to the skin, or, alternately, in a position of repose, or, "laid down" position oriented somewhat parallel to the skin describing a small acute angle in relation to the skin. This has been accomplished by those skilled in the art by use of various blends and compositions of various adhesive mixtures, chemical compounds, or, materials applied using various multistep complex methods employing a combination of variety of many types of applicators, instruments, tools, together with techniques of styling materials which traditionally accomplish application to the hair shafts by direct contact through various interrelated and interdependent multistep techniques of alternate wiping, combing, brushing, and spraying with various sprayers including aerosols, wet sprays; and, or, gels, together with combing, curling, rolling, and wrapping devices, respectively-some of which apply heat; and, or, two-stage "setting" or chemically interactive polymerizing and setting means. The object of methods of liquid or vaporous application is to encapsulate the entire hairshaft individually and collectively with a composition of liquid coating which will evaporate leaving a hardened solidified residue so as to render the hair shafts less flexible and able to move causing them to remain as positioned for an extended period and resist movement or change in position; and, in some instances (depending on the particular type of fixative used) increase, or, decrease infusion and diffusion; of, and migration of moisture into, through and over the hair. This is accomplished by various means which has traditionally been used by those skilled in the art by means of chemical agents to accomplish this by incrementally depositing successive layers of residual solids remaining from evaporated fluidized fixture or holding agents thus increasing the cross-sectional diameter and circumference of hair shafts in a somewhat evenly distributed homogenous coating of the entire hair shaft artificially by adding this incremental thin layer of semi-rigid coating of residual solids to the outer circumference of the hair shaft thus stiffening the hair shafts and contributing to their tendency to stand up and mutually adhere to each other. Desirable results have been obtained by use of volatile fluidized liquids, gaseous, vaporous or chemical substances acting as diluents or carriers for blended compositions consisting of compounds and mixtures of solids suspended and dispersed in them which during application, sublimation, and subsequent evaporative drying takes place evaporating the fluidized volatile liquid or gaseous components of the fixative or holding mixtures leaving the suspended solid components deposited on the collective hair shafts in a manner which results in a stiffening or hardening and immobility of the hair through a process of adhesive bonding; and, or, in some cases, partial chemical bonding which may involve partial cross-linking with various components of the hair tissue. This can in some instances be achieved by thermal means employing a variety of heat sources by direct contact, inductive, or convective means of heat transfer originating from a variety of types and designs of hand-held heating curling irons; and, or, hot air blowers which can be either hand-held or completely envelop the entire body of hair to dry, or, set liquid compositions of thermoplastic; and, or, thermosetting suspended solid particles of adhesive fixative materials.

2. Description of the Prior Art

Hair holding adhesives employing various means of apparatus, instruments, fluids and techniques using brushing, combing and heat have been used for many years to create useful and attractive hairstyles which accentuate the positive aspects of the users physical features. Haircare compositions are capable of altering facial characteristics of the person being styled. Hair can be "fluffed up" or "slicked back" through various means of "volumizing" or aggregating individual hair shafts collectively or by disaggregating them to produce a desired effect which can express the image desired by the person being styled.

Fragrances are often included in haircare compositions to impart desirable olfactory sensations for those in close proximity to the person styled. Insoluble hydrophobic and lipophilic waxy and oily materials as well as soluble hydroalcoholic aqueous materials are applied individually and in combination to provide desired appearances. These materials may contain emollients, lubricants, illuminants, fragrances, preservatives, moisturizers, plasticizers, emulsifiers, colorants and micro-biocides to impart desirable properties to the composition when applied to the hair in situ.

Because of the heterogeneous nature and phases of the anhydrous and hydrophilic components it is often necessary to liquefy and emulsify them using physical and chemical means to alternately disperse and intersperse them in desirable ways to produce the phase, viscosity, molecular weight and distribution of components throughout the composition in a homogenous manner through the use of mechanical mixing, melting, heat and chemical dispersing agents such as ionized, cationic or no-ionic surfactants.

HYDROPHOBIC VS. HYDROPHILIC

A hydrophobic material is insoluble in water and resists the passage or penetration of water into it or through it interstitially as in the "water-of-hydration". This is often due to the size and linking of the molecular structure in relation to the molecules of water. A hydrophilic substance conversely allows water molecules to penetrate, cling to it, or, pass through it interstitially. Water soluble or based cosmetics are said to be hydrophilic and often use humectants to preserve the moisture content of the composition to prevent it from drying out and becoming dysfunctional. Conversely, hydrophilic compositions may also employ anti-humectants to prevent the undesirable uptake or migration of ambient moisture from the atmosphere or elsewhere which can have equally undesirable effects by diluting the composition.

Hydrophilic substances are easily washed out and diluted by rain, moisture, or relative humidity whereas hydrophobic substances in cosmetic systems are more resistant to the effects of moisture and tend to be retained longer by the epidermal surfaces to which they are applied and resist being diluted and washed off by external moisture while acting as a film-like barrier and holding moisture in the epidermal or epithelial tissue to which it is applied.

In the instance of formulating a hairstyling composition I have discovered an anhydrous hydrophobic composition that is preferred over hydrophilic compositions as it resists ambient moisture in the air in the form of relative humidity and has longer stability in the fixed or styled position and is resistant to rain and washing as compared to aqueous or hydroalcholic hydrophilic compositions.

Another practice in the art of hairstyling is to use a liquid or semi-liquid hydroalcoholic aqueous soluble gel phase of liquid carried or suspended fixative or holding agents by dispensing them on to the hands of the hairstylist/applicant and applying them manually by means of the applicant's hands to rub the materials on the hair prior to, and during, subsequent desired positioning or sculpting of the hair to achieve a desired form or aesethically useful shape in the body of the hair being formed or styled.

These semi-solid gel-like systems and pomades have traditionally been hydrophilic compositions which are ordinarily miscible with aqueous extracts such as are found in essential oils, or fragrances, and other active ingredients such as biocidal preservatives and colorants. These hydrophilic components have contributed to rendering hair care cosmetic compositions somewhat stable for only relatively short periods of time.

However, disadvantages of hydrophilic hydroalcoholic aqueous compositions are that they tend to dry out over time and crumble as the interstitial "water-of-hydration" evaporates, thus destabilizing hydrophilic compositions and rendering the "shelf life" of the product less desirable. To overcome this problem of too little water or too much water being attracted to or transpiring from these hydrophilic compositions from ambient external relative humidity and moisture, it becomes necessary by those skilled in the art to include various "humectants or anti-humectants" in the composition to maintain a delicate balance of the interstitial "water-of-hydration" in the hydrophilic composition when exposed to a broad range of external relative humidity and temperature conditions.

Also, due to the hydrophilic properties of such compositions and the modification of their properties by ambient relative humidity, moisture and temperature conditions they are easily diluted and the effectiveness diminished when used as vehicles for applying active holding agents, fixatives and colorants to the hair. They can be easily diluted and washed out.

Solid hydroalcoholic aqueous hair care compositions have a tendency to dry out and limit their "shelf life" and physical stability whereas solid hydrophobic anhydrous cosmetic compositions composed principally of lipophilic waxes and oils last longer and have greater longevity in "shelf life" especially where they are comprised partially of organic components subject to breakdown by microbes.

Unless there are stable long-lasting humectants and anti-humectants such compositions can alternately attract or expel interstitial water-of-hydration depending on ambient environmental conditions of relative humidity, moisture and temperature.

Anhydrous hydrophobic systems are more desirable as carrier vehicles for dispersing or applying colorants, biocides, fixatives or emollients and once applied lipophilically tend to adhere better and longer to the natural sebaceous oils and fatty compounds found in and on epidermal and epithelial tissue such as hair and skin and are not easily washed out by ambient moisture such as rain, water, humidity or regular washing. A problem which hitherto prevented effective use of solidified hydrophobic systems of the type herein described has been the inability to adequately intermix, emulsify and alternately evenly disperse and intersperse in a stable manner a blend of heterogeneous hydrophobic components and heterogeneous hydrophilic components in a liquid phase ending up with a homogeneous solid phase of evenly dispersed components in the preferred composition. This has been accomplished in this process by a high shear thermo-mechanical bifluous emulsification process which alternately disperses and intersperses the heterogeneous hydrophilic components of the composition interstitially in a homogenous manner thixotropically within the homogenized emulsion of anhydrous hydrophobic components of the composition thus making it difficult for "water-of-hydration" to easily escape from the composition or ambient moisture to enter from external sources of high relativehumidity by the diffusion process or to seek equilibrium in a manner which will tend to destabilize the hydrophilic component by dilution and therefore be detrimental to the integral bonding of the entire composition. The use of a homogenized emulsified blend of heterogeneous hydrophobic components such as certain waxes and oils as the major vehicle to encapsulate the more diminutive volatile soluble aqueous components of active ingredients serves to create a differentially permeable moisture penetration into the composition.

By formulating anhydrous hydrophobic solid phased formulations into cosmetic compositions micro-organisms with a propensity to contaminate the proliferate within the organic fractions of the cosmetic are denied essential moisture to survive and multiply which can under certain circumstances inhibit their proliferation and infection of the applicant and host to which the cosmetic composition is applied.

This process and preferred anhydrous hydrophobic composition allows lower concentrations of less active ingredients to be used or not wasted during production, use, or, application by diminishing the prospect of dilution as when an alternate or straight hydrophilic composition is used and applied in an aqueous aerosol or spray.

SUMMARY OF THE INVENTION

The present invention corresponds to long lasting physically stable cosmetic compositions having little or no water. These cosmetic compositions comprise hydrophobic lipophilic materials as the principle vehicle carrying the active ingredients in a continuous solid phase.

The hairstick in combination with the apparatus described herein in the preferred sanitary composition and embodiment used to sculpt, style and hold hair in place in situ while extending the "shelf life" and stability of the composition and minimizing microbial infection, or cross contamination comprises:

a. a process for manufacturing the preferred composition
b. use of a preferred container/dispenser/applicator apparatus to dispense the preferred composition in combination with a technical method of artfully applying the preferred composition.
c. a preferred composition comprised of
  (1) the solid continuous phase of hydrophobic lipophilic components which are not less than 30% nor more than 60% of the preferred composition
  (2) natural and synthetic liquid hydrocarbon oils combined which do not comprise less than 15% nor more than 35% of the preferred composition.
  (3) the solid wax part of the composition is not less than 35% nor more than 50% of the preferred composition.
  (4) the entire preferred composition does not have a binder/plasticizer/coupling agent exceeding 5% of the preferred composition.
  (5) the preferred solid composition has moisturizers collectively comprising not less than 20% nor more than 45% of the preferred composition.
  (6) microbial biocides collectively comprising no more than 2% of the preferred composition. (7) a solid wax based composition in which the combination of fragrances, colorants and preservatives collectively comprise not less than 5% nor more than 10% of the preferred composition.

DESCRIPTION OF THE PREFERRED EMBODIMENTS

Figure 1:
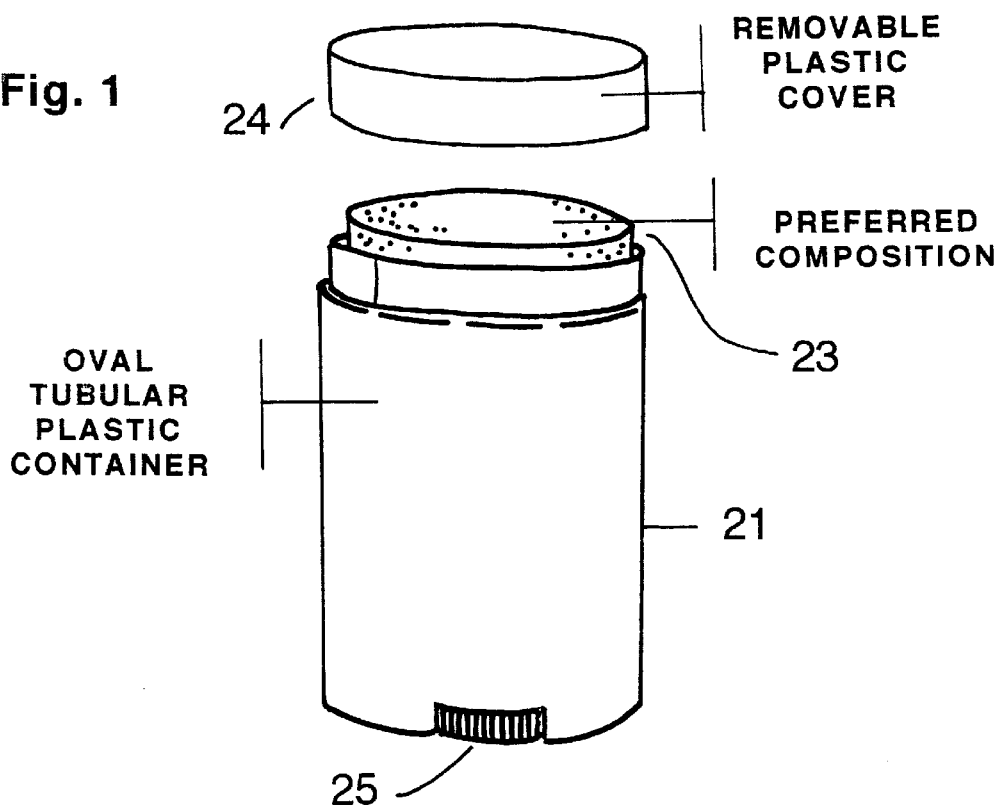
FIG. 1 illustrates the hairstyling stick of the invention.

Components utilized in the present invention are described in detail below. All percentages are by weight.

Lipophilic Materials

In the preferred composition lipophilic materials comprise not less than 90% of the preferred composition. These include both solid and liquid materials known in the art.

Liquids

Liquids comprise 20–35% of the preferred compositions. By liquid it is meant material that flows at ambient room temperature between 60–80° F. These liquids are derived principally from hydrocarbon oils produced from both organic sources and inorganic mineral sources and mixtures thereof. Hydrocarbon oils useful in the preferred composition are rapeseed oil. theobroma oil, castor oil, jojoba oil, mineral oil, silicone oil and various fragrances and essential oils. Hydrocarbon oils derived from natural sources such as plants contain components of fatty acids such as are in castor oil, rapeseed oil, jojoba oil, theobroma oil and various essential oils and fragrances.

Hydrocarbon oils derived from mineral sources are also used in the preferred composition that are comprised of petrolatum, mineral oil and silicone oil (dimethicone copolyol) and mixtures thereof.

In the preferred compositions the hydrocarbon oils are comprised as follows:
  a. petrolatum from 15% to 30%
  b. rapeseed oil from 4% to 8%
  c. theobroma oil (cocoa butter) from 5% to 8%
  d. castor oil from 2% to 5%
  e. jojoba oil from 2% to 3%
  f. mineral oil from 3% to 10%
  g. silicone oil (dimethicone) from 1% to 2%
  h. essential oils (fragrances 1% to 2%

Solids

Hydrocarboniferous hydrophobic lipophilic materials in solid form comprise not less than 35% nor more than 50% solids. By solid it is meant the material is firm and doesn't flow as a fluid at ambient room temperature such as 600–80° F. but can be plastic or elastic. These wax-based solids have melting points ranging from 50° C. to over 90° C., individually, and in mixtures thereof. For the hydrocarbon material to be further classified as a solid the carbon chain is longer in solid phases than liquid phases and said to have a higher molecular weight as a result. A wax said to have a high molecular weight may exhibit solid characteristics while the same wax said to have a low molecular weight may exhibit liquid flowing characteristics.

The solid waxes selected in the preferred composition consist of the following:
  a. paraffin (eskar) not less than 15% nor more than 20% of the preferred composition.
  b. microcrystalline wax not less than 10% nor more than 20% of the preferred composition.
  c. beeswax not less than 5% nor more than 15% of the preferred composition.

Moisturizers

The preferred composition of the hairstick is composed of various moisturizers combined and dispersed in the continuous solid lipophilic phase and are comprised of:
  a. petrolatum comprising not more than 30% nor less than 15% of the preferred composition.
  b. mineral oil comprising not less than 3% nor more than 10% in the preferred composition.
  c. castor oil comprising not more than 5% nor less than 2% in the preferred composition.
  d. jojoba oil comprising not more than 3% nor less than 2% in the preferred composition.
  e. dimethicone copolyol (silicone oil) comprising not more than 2% nor less than 1% of the preferred composition.

Coupling Agents

In the preferred composition coupling agents and plasticizers are used in addition to thermo-mechanical excitation to liquefy and blend the thixotropic components of the composition to homogeneously blend the heterogeneous hydrophilic soluble components with the hydrophobic anhydrous insoluble components of the preferred composition. To accomplish this castor oil is used as a binder/plasticizer to resist moisture and oxidation in combination with beeswax to prevent crystallization of the fatty components present in the preferred composition. Beeswax also exhibits lipophilic properties which have an affinity for attracting and binding the preferred composition to the sebaceous oils of the epidermal and epithelial hair and skin of the scalp.

Additional Ingredients

The preferred hairstick composition described herein can contain additional ingredients known and commonly used in the art for cosmetics.

Among the additional ingredients that are used are preservatives, conditioning agents, emollients, lubricants, illuminants, biocides such as germicides, fungicides, bactericides and viricides and extenders in addition to skin and hair conditioners used in the preferred composition. Petrolatum, mineral oil, dimethicone, rapeseed oil, castor oil and cocoa butter (theobroma oil) and jojoba oil all fall into this group of epidermal and epithelial conditioners used in the preferred composition described herein.

Active Ingredients

It is also the practice in the art of formulating cosmetic compositions to generally include certain active trace additives to liquid formulations; and, compositions to include preservatives in the composition for purposes of lengthening effective shelf or storage life, impart shine, or gloss, to the surface of the hair to which it is applied by reflecting and refracting light which highlights the hair in an aesthetically desirable, useful and attractive way. Also, it is the practice in the art to add other trace substances to resist or attract moisture usually referred to as antihumectants, and, or, humectants, respectively, and add nutrients or various other medicinal or odoriferous aromatic blends of fragrances which impart other properties such as color to the body and individual shafts of hair.

Preservatives

A traditional and desirable practice in the art of formulating desirable compositions of haircare cosmetics has been to include preservatives that are germicidal, bactericidal and fungicidal not only to prevent breakdown of compositions comprised of organic derivatives from the cells of living organisms which are mixed or blended with inorganic mineral-derived substances such as hydrocarbon additives while being non-irritating, non-toxic, non-allergenic to subject hosts such as hairstylists and their subjects to which the cosmetic hair care compositions are applied, especially to the epidermal tissues, epithelial tissues, and soft, moist, mucous membranes. It is also desirable in the art to produce cosmetic compositions for hair, and, epidermal contact which will not permanently stain tissue and which can be removed by ordinary washing with aqueous detergents.

Most preservatives and traditional medicinal additives have historically been included in certain liquid cosmetic compositions of "fixative" or "holding" agents at concentrations to only just inhibit or control certain yeast or mold fungi; and undesirable bacteria which can migrate, invade, multiply, and detrimentally reside in some of the substrate components derived from the organic extracts of the cells of living organisms used in liquid blends of fixative compositions. Yeasts are a class of fungi which are budding solitary micro-organisms that appear smooth and pasty in texture and are creamy white, while molds are filamentous drycolonies of fungi. The flowering mycelium of molds exhibit a white cotton-like appearance and produce and expel the reproductive spores which can parasitically invade or infect plant and animal organic tissue or its derivatives and damage it by producing enzymes which break down the organic material to produce vital nutrients for the mold's survival, reproduction and proliferation. These microbial microorganisms and other vermin attracted to organically-derived components of cosmetic compositions produced from the cells of living organisms comprising liquid cosmetic compositions and can after prolonged continuous contact also irritate the skin of the stylist applying these compositions with their hands and be transmitted from one host subject being styled to another subsequent host subject to be styled by the same stylist if sanitary antiseptic precautions and treatments are not followed by sterilization of implements such as combs, hands, scissors, brushes, rollers used to apply these materials. Although many of these haircare cosmetic compositions may contain certain fungicides and antiseptic germicides and bactericides to control or inhibit growth and multiplication of certain germs, bacteria, and fungi in the form of yeasts or molds to act as preservatives in the compositions when exposed to the micro-organisms for a long period of time they are usually not concentrated enough or broadly toxic enough to act as broad-based general "contact" biocides to instantly kill migrant microbes which may only be contacted briefly during cross-contamination from shared cosmetics or be toxic to strains which may be airborne or occur in or on the host such as resistant viruses like HIV harboring in body fluids.

Preservatives are used in cosmetics to protect against infection during use and prevent decomposition of a cosmetic product comprised of organically-derived vegetable or animal extracts subject to microbial multiplication from germs, fungi, yeast, bacteria or viruses. The presence of water and various organic components such as beeswax, rapeseed oil, cocoa butter, jojoba oil and castor oil such as are used in this preferred composition can combine to create an environment and substrate of vital microbial nutrient materials which under certain conditions of temperature and moisture can reproduce, multiply and proliferate undesirable microbes in the absence of appropriate concentrations of preservatives and biocides. Cosmetic users unintentionally introduce germs and various microbes into open containers of cosmetics that may otherwise exhibit or present no evidence of contamination until the contaminated cosmetic comes in contact with the user and causes an infection. Cosmetic preservatives should be actively effective at a low concentration against a wide range of micro-organisms over a wide Ph (acid/alkaline) range as well as be compatible with other ingredients in the composition and be non-toxic, non-irritating and non-sensitizing or non-allergenic to the applicant/stylist and host to which the cosmetic is applied. Preferably a preservative should be colorless, odorless and chemically stable as well as economically and easily formulated into the product. Parabens are widely used as well as alcohols and essential oils. Methylparaben (methyl p-hydroxy benzoate) is one such preservative widely used in the preferred composition described herein which is an antimicrobial preservative comprised of small odorless, non-toxic, colorless crystals.

Propylparaben (propyl p-hydroxy benzoate) is another widely used preservative and biocide used in the cosmetic industry against both bacteria and fungus. This group of paraben preservatives, which are active against a variety of organisms, are neutral in Ph, low in toxicity, slightly soluble, and, can remain active across a broad spectrum of alkaline, neutral or acidsolutions. They are used medicinally to treat fungus infections.

Triclosan (Irgasan DP 300 $C_{12}H_7CL_3O_2$) is a broad spectrum diphenylether anti-microbial agent used as a preservative and disinfectant which has been shown effective against many bacteria for over a decade and more recently been shown to be effective as a contact biocide on viruses as well such as HIV when used in concentrations up to 2%.

Triclosan when used with the parabens in a cosmetic compositions containing both organic and inorganic compounds may have synergistic, antiseptic and biocidal properties.

Essential Oils

It is a desirable to include preservatives in formulating cosmetic compositions which have been derived from vegetative sources by dissolving plant tissue in various solvents and then distilling these compositions to form hydroalcoholic aqueous extracts or "essential oils" which are in a liquid form which must be included into cosmetic compositions. Many of these extracts in addition to being biocidal or antiseptic to certain germs, fungi, or bacteria also emit a diffusive aromatic fragrance which has desirable olfactory sensations of fresh flowery medicinal fruity sweetness on subjects to which various cosmetics are applied which have these preservatives included. It is desirable and useful to include blends of these aromatic fragrances that have a combination of attractive fragrant properties as well as ancient antibiotic biocidal properties and are non-toxic, or, non-allergenic to subject hosts to which the cosmetic is applied. These fragrant oils can be blended with liquid carriers or waxes by use of strong emulsifying agents which may be ionized or non-ionized. Many of these natural preservatives, however, are not effective, toxic, or useful in controlling or destroying the much smaller viruses which are known to sometimes invade, exist, reside, and linger in body fluids where they may multiply and migrate to and from epithelial or epidermal tissue which like the other bacteria, germs, or fungi can be picked up and transmitted during brief contact thus cross-contaminating other hosts which may be subsequently contacted briefly by the instruments, tools, hands, and products being used during the ordinary course of hairstyling operation on multiple subjects by stylists.

Essential oils are preservatives that are ancient. They impart desirable aromatic fragrances and are obtained from plants through a variety of extractive processes. Most essential oils produce the taste and fragrance of the plant from which it was extracted. Most essential oils are volatile and easily vaporized at ambient temperatures. A substantial number of essential oils have antiseptic, germicidal and preservative effects as well as desirable fragrances. They were called "essential" as they were believed to be medicinally essential to life by the ancients and considered to be the "essence" of the plant from which they were derived. They usually have no known toxicity to skin when used in small concentrations. The fragrance used in the preferred composition was an extract of honeysuckle.

Only nature can produce whole essential oils. These oils are tiny droplets contained in glands, glandular hairs, sacs and veins of different plant parts such as leaves, stems, bark, flowers, roots and fruits. They are the essence of a particular plant form and give it its uniquescent. Essential oils protect plants from invasive micro-organisms and have been found to help humans similarly. When applied to the epidermal tissue in dilute concentrations they exhibit antiseptic properties and tend to prevent, inhibit and heal infections. Essential oils are volatile and easily sublimate from a liquid to a gas at room temperature. They aren't oily but rather a water-like fluid. They are the exclusive product of extraction of the volatile aromatic fractions contained in the substances bearing their name. They are a highly concentrated form of the plant part from which they are derived. Essential oils represent 0.01%–10% of the plant with the average found in most aromatic plants to be approximately 1–2%.

Essential oils are extracted from plant parts through a variety of processes not the least of which is a steam distillation process by forcing steam into the vegetative material through the bottom of a closed vessel containing the vegetative plant matter which rests on a grid or stack of trays ruptures the cells and carries the oils off in a vapor that is cooled, condensed and further distilled into concentrated oils. Essential oils are also squeezed or expressed from plants when it is determined that the steam distillation method will alter their composition undesirably. Expression is a controlled squeezing process (by hand or machine) used exclusively for citrus fruit peels. The resulting oils are not completely volatile, but are acknowledged as essential oils and can be used as they occur in nature. Solvent extraction is also used to extract scented concentrates called resinoids, concretes, absolutes and pomades to develop perfumes, pharmaceuticals and other commercial products such as flavorings. Absolutes are extracts that are entirely alcohol soluble and are used to formulate perfumes. They are obtained by alcohol extraction of concretes which are first obtained by treatment of the plant material with a hydrocarbon solvent such as hexane or ether. In the solvent extraction process plant material is mixed with various organic solvents such as alcohol, benzene or hexane to extract soluble plant molecules. Use of alcohol as a solvent produces hydroalcoholic extracts called absolutes or tinctures. When benzene, hexane or ether is used as a solvent they produce resinoids and concrete. Concretes are extractions from flower or plant materials that have been treated with a hydrocarbon solvent. Resinoids are also hydrocarbon-solvent extracts of plant material, but unlike concretes, resinoids are obtained from previously non-living, non-cellular plant materials such as balsams, gum resins, natural resins and oleogum resins. When oil or fat is infused into the plant parts infusion oils or the process called Enfluerage is practiced. The highest grade of essential oils is obtained from distillation and expression processes. Enfluerage is a form of solvent extraction whereby the plant's floral parts are layered onto fat in several layers. Over time and many layerings the fat absorbs much of the scented molecules. Since some plants have low essential oil content and other methods would destroy these fragile essences, this method has certain advantages. The ancient Egyptians used this method to make scented unguents and various cosmetics.

It is also desirable to formulate hair-protective additives into compositions which will protect hair shafts and body of hair by creating a barrier to invasive damage from external contaminants, pollutants, and damaging effects of sunlight ordinarily occurring in the atmosphere, or, water to which hair is ordinarily exposed such as various acids and metal ions.

Aerosol application of vaporous fluids is becoming increasingly less desirable as a means for application due to environmental contamination by certain ambient interactive gases such as fluorocarbons used as vehicles for fluidized concentrate propellant carriers of various liquid fixatives, holding agents, and haircare products which during application arbitrarily release random uncontrolled wasteful ambient volatile oversprays of odious pollutant gaseous vaporous solvents and solids into the atmosphere which cannot be avoided or recovered during normal application and some portion of these noxious gaseous vapors are inevitably inhaled by hairstylists and subjects to which the product or composition is being applied in several stages, or steps, during the ordinary course of application in the hairstyling processes that use such liquid or fluidized vaporous compositions. Many aerosol compositions have also been found to be very flammable. Also, these released oversprays of fluorocarbon gases have been found to cumulatively be detrimental to the atmosphere, particularly the ozone layer breakdown and contribute adversely to global warming.

Use of organic chemicals derived from renewable natural resources such as vegetative, herbaceous, or woody plant sources are conversely becoming increasingly more desirable for use in cosmetic production: and, by consumers of haircare products due to their perceived lower impact on the environment, biodegradability, and renewability of the natural resources they are derived from compared to the increased cultural stigma discouraging use of more traditional ingredients derived from mining non-renewable inorganic mineral or fossil fuel resources such as petroleum, coal or natural gases used in the formulation of carboniferous organic hydrocarbon compounds or compositions derived from animals or human sources such as lanolin, cutin, collagens, or hair keratin protein which is derived from human hair.

An undesirable occurrence in the application of holding agents or fixatives of haircare compositions ordinarily used for hair styling has been contamination through direct contact of applicants hands, brushes, combs or inhalation of sprays during application which requires considerable time to apply and set or cure and clean up and sanitize afterward.

Sanitizing instruments, tools, and implements used by hairstylists after application and between subjects styled is time consuming. Also, considerable time is required in the multistage process to apply, curl, wave, set, cure, and sanitize these instruments afterward between subjects when liquid hair care products are used. Also, existing government cosmetological licensing regulations are being more strictly enforced regarding sanitary procedures used by hairstylists and salons to minimize cross-contamination, shared cosmetics and transmittal of microbial microorganisms which carry disease and can be carried from one host to another by contact of unsanitized instruments, tools, or, manual contact such as with certain germs, fungi, bacteria and viruses. Many cosmetic formulations only include biocides which are passively toxic after prolonged exposure to germs, fungi, and bacteria (which tend to break down the composition and limit shelf life) without including higher concentration of contact antiseptic compositions which are toxic to, or, inhibit transmittal of viruses such as HIV on contact. It is a practice within the art of formulating cosmetic compositions to include biocides which are toxic to various microbial microorganisms which although they may be toxic or inhibitive over time in certain low concentrations to the several microorganisms (such as Gram Positive or Gram Negative bacteria) for which they were designed to inhibit or destroy after prolonged contact without being toxic to the subject or detrimental to the host to which the cosmetic is to be applied. Bacteria are differentiated by a "gram stain" which demonstrates a difference in the cell walls of these two broad groupings of bacteria. A "gram negative" bacteria has a thinner, double membranous wall structure susceptible to antibiotics, while "gram positive" bacteria have a thicker, structureless cell wall which is more resistant to physical disruption. Although transmittable viruses have been an issue for many years there has been no regulatory requirement to include viricides in cosmetic compositions nor has there been up until recently adequate compatible viricides available nor have they been included in commercial wax-based haircare compositions, more especially blended anhydrous hydrophobic lipophilic solid wax-based compositions comprised, in combination, with animal, vegetable, or mineral-derived oils or heavy molecular weight waxes used in haircare fixatives or "holding" compositions for hairstyling as a carrier for active ingredients which collectively represent less than 20% by weight or volume.

It is also desirable in the art of formulating cosmetics to use blends of various waxes, some of which are derived from mineral sources and some from living sources such as plants and animals. Certain of these waxes are hydrophobic and resist absorption or adsorption of water or aqueous solutions. These are generally higher molecular weight waxes having larger molecules which inhibit their penetration of epidermal or epithelial tissue by creating a barrier to penetration of aqueous solutions while other waxes which are desirable to be used are a lipophilic group of phospholipids containing linoleic and linoleic acids which have certain benefits to epidermal tissue part of which are attracted to certain proteinaceous fatty acids found in epithelial tissue and the other parts of these lipophilic waxes and oils are hydrophilic and are attracted to the water components of living epithelial tissue. It is desirable to include both the hydrophobic waxes and hydrophilic extracts in cosmetic compositions due to the respective beneficial properties they impart respectively. However, their miscibility has been a problem due to having little affinity for each other respectively due to their hydrophobic and hydrophilic properties, respectively. Liquid phases of these waxes, oils and extracts require special emulsifying techniques and chemicals to achieve this.

Colorants

Colorants are widely used in cosmetics. They are derived from both natural and synthetic origins. The FDA designates color classes by the initial F, D, and C. A designation of FD & C denotes the colorant is approved for use in food, drugs and cosmetics. A designation of D & C means the colorant may only be used in drugs and cosmetics. Colorants useful in the preferred composition are F D & C approved dyes, pigments and mixtures thereof.

In the manufacture of cosmetics, colorants are selected by those skilled in the art that are safe, stable and attractive to the potential user of the product. These dyes or colorants are comprised of organic, inorganic and, or, synthetic components. Inorganic components of these colorants used in the preferred composition were selected from a group consisting of micas, iron oxides and titanium dioxide, treated pigments and mixtures thereof.

Inorganic mineral colorants used in this preferred composition are iron oxide, titanium dioxide and mica. Iron oxide imparts red and brown hues. Iron oxides vary in color from red to brown, black to orange or yellow depending on the degree of water added and purity. These produce colors such as ocher, sienna and iron oxide red. Titanium dioxide is a "whiting" agent and the interspersed mica produces pearlescent iridescence by reflecting and refracting light. Other chemical colorants utilized in the preferred composition are D & C yellow #1, D & C yellow #2, D & C red #17. D & C green #6 in mixtures thereof.

The FDA assigned numbers to the various dyes after certification of specific formulas which have been tested and approved. D & C yellow #1 contains one atom of nitrogen and two of oxygen and is one of the "nitro" dyes that is synthesized from coal tar that is FDA certified. It is used to impart a gold color. D & C violet number 2 or Alizurol Purple SS. Solvent Violet 13 is classed chemically as an anthraquinone color that imparts a dull bluish violet when used in combination with other colorants in the preferred composition. D & C red Number 17 or Toney Red is classed chemically as a diazo color. It is used in the preferred composition to impart reddish hues. D & C Green Number 6 or Solvent Green Number 7 is a dull bluegreen color and is classified chemically as an anthraquinone color and is used in combination with other dyes listed to achieve particular hues and desirable color tones in the preferred composition.

Colorants are dispersed in liquid medium prior to addition to the preferred composition. Colorants can be purchased already dispersed in a medium or as dry powders to be dispersed by the formulator in a medium of choice.

The combined percentage concentration of colorants in all of the preferred compositions described herein do not exceed 1.5%. Individual colors are varied using all of these colorants to produce preferred colors which are silver, gold, brown, red, purple having a desirable metallic iridescent pearlescent property imparted by the fine particles of mica interspersed at a rate of 3–5% throughout the compositions.

An undesirable feature of trying to apply uncolored, or, so ∓called "neutral-colored" wax-based hair care compositions to hair has previously been the apparent observable residual opaque flakes of residue comprised of white opaque solids or fixative materials which contrasts dramatically in an aesthetically undesirable unfashionable appearance with darker colored hair to which it may be applied.

I have discovered by including color coordinated and enhancing colorants comprised of those referred to above in varying concentrations to provide certain uniquely useful and aesthetically desirable and proprietary colors can be incorporated into the preferred compositions. They are: silver for gray hair, gold for blonde hair, red for red hair, brown for brown hair and violet for black hair. All of the colors formulated for use in these preferred compositions exhibit metallic-like iridescent, pearlescent properties which reflect and refract light randomly. This is made possible by the mica dispersed evenly in the colorants.

Solid Phase vs. Liquid or Aerosol

I have discovered by changing the phase of the combined preferred composition of wax, oil and soluble components used as a fixative for styling through increasing the specific density of the composition substantially until it becomes high enough to be transformed from a liquid to a solid phase of the wax-based carrier to where the composition is of much greater specific density and molecular weight and becomes a solid having higher specific gravity and higher melting point with a resulting lowered percentage concentration of additives (as a percentage of volume and weight) as compared to more traditional concentrated aerosol or vaporous sprays, liquids, vapors, or gels, respectively, having fewer active ingredients(as a percentage of weight or volume) which holds the hair in place as compared to the more established traditional multi-step consecutive process that totally encapsulates the hairshafts with liquid carried fixatives; and, then, through a process of sublimation and evaporation sometimes accelerated by heat—evaporate the volatile components of the fixative or holding fluid or liquid carrier leaving the residual solids of active ingredients attached to the hair by various surface-bonding methods to perform their respective functions.

Various waxes, oils and solutions both organic and inorganic are used in combination to impart various desirable properties in the preferred composition. The inorganic waxes used in this composition consist of paraffin (eskar) and microcrystalline wax which comprise 30–40% of the composition and act as a solid phase carrier vehicle for the other active ingredients. Paraffin is a distillate derivative from wood coal, petroleum or shale oil. It is colorless, odorless and greasy. It easily melts over boiling water and is harmless to the skin.

Microcrystalline waxes are various plastic materials derived from petroleum and differ from paraffin waxes in that they have a higher melting point, higher viscosity and much finer crystals that can only be seen under a microscope and have no known toxicity. One such microcrystalline wax is marketed under a registered trademark called Ceresine and is referred to as "earth wax" and is a white or yellow hard, brittle wax derived from the purified hydrocarbon ozokerite.

The organic natural beeswax derived from virgin bees is employed in the preferred composition as an emulsifier, binder and coupling agent. It is practically insoluble in water. It is yellow and soft to brittle.

I have discovered a means for effectively applying a holding or fixating agent to hair in situ with the use of less concentrated active ingredients as a percentage of total weight and volume in a solid phase of an anhydrous hydrophobic wax-based emulsion.

Inorganic Oil-Based Derivatives

Certain mineral-based oil derivatives such as petrolatum (petroleum jelly) and mineral oil impart certain desirable properties to the preferred compositions. These components together comprise 25–35% of the total preferred compositions. Petrolatum known usually by the tradename Vaseline or generically as petroleum jelly or paraffin jelly is a non-toxic purified mixture of semi-solid hydrocarbons derived from petroleum. It is yellowish to light amber or white, semisolid unctuous mass that is practically odorless and tasteless, and almost insoluble in water. It is used in the preferred composition described herein, together with the other waxes to add body, impart shine and produce a smooth texture. It is a smoothing lubricating emollient to epidermal and epithelial tissue which holds moisture in the tissue to which it is applied.

Mineral oil or "white oil" is also a lubricant, protective agent and binder which adds brilliance and, or, shine and also acts as an emollient. It is a mixture of refined liquid hydrocarbons derived from petroleum. Like petrolatum, mineral oil also acts as a moisturizer which helps create a film to impede evaporation from epidermal or epithelial skin tissue. It is hydrophobic or water repellent substance like petrolatum, paraffin, microcrystalline waxes and beeswax.

Mineral oil is non toxic, colorless, transparent, odorless and tasteless, and, when heated, smells like petroleum and coats the surface of epidermal and, or epithelial tissue without any penetration and leaves a shiny protective surface.

Dimethicone or copolyol is an inorganic silicone oil with low toxicity that is white and viscous and is formulated into the preferred composition as an ointment base or topical medicinal vehicle as a skin protectant, hair conditioner and emollient.

Organic Oils

Rapeseed oil, cocoa butter, castor oil, jojoba oil are all combined in the preferred composition to impart certain desirable properties as a lubricant and illuminant. Rapeseed oil is a brownish yellow oil derived from a turnpike annual herb of European origin which is grown as a forage crop for sheep.

Castor oil or Palm Christi Oil comes from the seed beans of the castor oil plant by expression. A form of polyethylene glycol is further refined from this oil and comes in molecular weights ranging from 3–200 with the range varying from a liquid at the low end to a solid at the higher end. It was incorporated into the preferred composition as a binder and plasticizing agent and softener which improves resistance to moisture and oxidation. It forms a tough shiny film when dry.

Cocoa butter or Theobroma oil was formulated into the preferred composition as an emollient to soften and lubricate the hair. Cocoa butter is a solid fat expressed from the roasted seeds of the cocoa plant which melts at body temperature.

Jojoba oil is extracted from the beanlike seeds of the desert shrub Simondsia Chinensis. It is a liquid wax formulated in a 2–3% consistency into the preferred composition as a hair conditioner with moisturizing and lubricating properties.

By reducing the percentage of the active ingredients to a small percentage concentration and changing the phase through the use of thermal-mechanical excitation which interstitially disperses and thixotropically emulsifies the liquid and solid phases of non miscible hydrophobic and lipophilic waxes, oils and hydroalcoholic aqueous soluble extracts of flowering plants into an invert emulsion having thixotropic properties to a continuous solid phase of a more dense heavier molecular weight blend of anhydrous hydrophobic and lipophilic solid wax compositions having certain desirable and synergistic antiseptic preservative and adhesive properties added; and, encasing the preferred emulsified composition and embodiment of the solid hair fixative composition in a tubular or cylindrical container/dispenser/applicator apparatus that is open on one end to permit graduated extrusion by mechanical means in measured amounts of the encased solid fixative or holding composition out of the open end of the tube as it is used up and sloughed off the solid wax embodiment of the carrier diluent and applied to the hair in situ in a certain rubbing or wiping motion when held in the hands of the hair stylist or applicant. When using this preferred composition in combination with the described preferred container/dispenser/applicator in a certain stroking motion outward from the base of the hair roots toward the ends of the hairshaft (in relation to the skin) the hair can be aggregated and laid down in a position of repose describing a small acute angle which can control "frizzy" or loose split ends in a manner that causes individual hairshafts to be mutually adhered to each other while radiating reflected and refracted light in such a manner so as to create a desirable and attractive lustrous gloss or iridescent pearlescent shine without adding substantial additional weight to the body of the hair collectively. By using the same apparatus and preferred composition and embodiment in combination, together with an inward stroking motion from the outer ends of the hair shafts toward the base of the root of the hair shafts toward the skin a uniquely useful and attractive desirable disaggregating volumizing effect and appearance can be achieved which causes individual hair shafts to become oriented upward describing a large acute angle in relation to the skin while also radiating reflected and refracted light which highlights the body of the hair in a uniquely aesethically desirable and useful stylized attractive design or appearance without adding substantial weight to or stiffening the overall body of the hair. Uniquely desirable, aesthetic and useful designs and attractive stylized appearances can be achieved in the body of the hair's appearance by combining use of the preferred embodiment of the applicator apparatus and preferred composition in this manner and technique of application. By only partially encapsulating randomly in a discontinuous coverage of only part of the hair shafts several uniquely and useful desirable and attractive aesthetic effects in design and styling can be created which are not possible when the hair shaft is completely encapsulated using liquid or aerosol fixative and holding agents. This partial encapsulation created by using the solid material of the preferred composition in application causes a random "skipping" application of the sloughed off or eroded solid wax-based carrier delivering the dispersed active ingredients together with the particulates of the solid wax-based carrier along the hair shafts which can cause part of the shaft to remain stiff while the other part of the shaft to which the preferred composition is not applied remains flexible thus creating very special, useful, and desirably aesthetic and attractive styling effects. When the base is coated from the root of the hair shaft partially up the hairshaft the hair can be caused to stand up more-or-less erect in a disaggregated fashion while the ends remain flexible. When hair shafts are coated with the preferred composition for some distance from the base or root of the individual hairshafts out toward the ends of the shafts then the base of the hair remains flexible and the ends become rigid or stiff creating uniquely desirable, attractive and useful stylized appearances and styling effects.

The preferred outer dispenser (container/applicator) encasing the preferred embodiment of the apparatus containing the solidified preferred composition of the hair fixative carrier acts as a sanitary prophylactic barrier as well as a holder of the preferred composition in the hands of the applicant for applying the solid hair fixative composition stick or embodiment to the subject's hair being styled. When wiped across the hair in a stroking motion the solid material carrying the active ingredients are eroded or sloughed off the preferred composition of the parent material of the solid wax embodiment and deposited and disposed on, and, left adhering to individual hair shafts in a random discontinuous "skipping" action which randomly applies the residual particles unevenly and incompletely, or, only partially coats or encapsulates various parts of the hair shafts unevenly in a random discontinuous uneven manner to produce uniquely useful and aesthetically attractive desirable styling and design effects and style that can't be otherwise obtained with total encapsulation by liquid phase fixatives or holding agents depending upon the messier, more time-consuming, more complex, stepwise consecutive processes requiring, alternately, curling, combing, brushing, heating, wetting, drying etc. The process which deposits or causes the solid wax-based carrier to slough off particles from the parent solid material of the preferred composition to be deposited on the hair shafts in the manner described is accomplished by the preferred composition which has a temperature related softening point such that when the preferred composition in the preferred embodiment apparatus is applied with pressure to the hairshafts the resultant friction generates an adequate amount of heat together with the body temperature at the surface of the solid body of the preferred composition which, in turn, softens the preferred composition breaking the bonds holding it together as a solid causing it to be separated in particulate form from the parent body of the solid wax-based composition and due to the particular adhesive component of the composition the sloughed off or eroded lipophilic particles cling to or adhere to the hair shafts as described above. This adherence is caused by a process of molecular, electrostatic and hydrogen bonding created by the heat and pressure and friction in the application process similar to bonding of cellulosic fibers under heat and pressure to form paper. This affinity for attractive physical bonding occurs on the surface of the hair shafts and through partial penetration of the hair shaft depending on duration and time the preferred composition and embodiment is in contact with the hair shaft and the amount of pressure applied. This bonding can further be enhanced by the subsequent application of heat to the treated hair through hot air blowers or heated contact curling irons used in hairstyling. This is accomplished by use of the preferred composition of the solid wax-based carrier and its active ingredients selectively coating the hair and causing it to be strengthened by increasing the diameter of individual hair shafts and mutually adhering to other hair shafts. This random discontinuous, partial application of a solid wax-based preferred composition having a lesser percentage of active ingredients(as a percentage of weight or volume) has several advantages which include the economics of producing a hair fixative holding product with less of the more expensive trace additives which tend to be more expensive than is required to achieve the same results when using liquid, aerosol, vaporous, or immersion techniques of fluid or liquid application which can become a competitive advantage in costing or pricing of the product in relation to the other more traditional previously used and traditionally accepted or approved techniques of application. This method is also faster with fewer steps and cleaner, less messy, more sanitary and environmentally friendly than previous, more traditional types, of application requiring more sequential complex steps in the application and setting process required to style and sculpt hair.

A unique styling property that the combination of this method of application together with the solid fixative product described above with the tubular-sleeved embodiment is that due to the partial, discontinuous, selective application to the hairshaft of the wax-based product can cause the base of the hair shaft to remain stiff while allowing the ends to be flexible which presents a desirably different and uniquely stylized attractive and useful appearance. Conversely, when the preferred embodiment is used to selectively apply the solid wax-based fixative agent to the ends of the hair it can be used to smooth and control split ends and frizzy hair and "slicken" or "sleek" down hair to produce a "slicked-back", shiny appearance. I have discovered that by adding certain metallic-like colorants to the solid formulation of the preferred composition of the waxed based carrier or diluent such as gold, brown, blue-black, and certain shades of red which are color enhancing and coordinated to match and highlight the color of hair to which the fixative composition is applied that it is an improvement over other singular opaque neutral-colored solid embodiments of fixatives that tend to leave undesirable contrasting flakes of solid material when applied to colored hair.

I have also discovered that by use of an oval or flat-shaped tubular sleeve in combination with the solid fixative agent to coat the hair in a wiping, brushing rubbing motion in the various techniques described above that the fixative can be applied in a more controlled manner to a wider strip or swath than by use of other traditional means during application similar to a broad brush for applying liquids but without the need or disadvantages of bristles that tend to comb the hair thus separating the very individual hair shafts which are to be bonded together with the fixative holding product to achieve the desired sculpted, volumized or "slicked-back" or "slicked-down" appearance desired. This method of application together with the higher concentration of a broader-based combination of preservatives eliminates the need for subsequent sanitary antiseptic cleaning the teeth or bristles of a comb or brush ordinarily required to remove the residue of the fixative in the instance of application of liquid fixatives or holding agents for sanitary purposes not required by the preferred embodiment described above. The preferred embodiment does not require dipping into a liquid or fluidized vaporous fixatives such as is required by a comb or brush and has little or no wasted overspray or unused or wasted residual material as in the use and application of liquid spray, aerosol, or vaporous applicators. It also has less contamination to the hands of the applicant during application.

Bifluous Thermo Mechanical Intermixing

Because a hydrophobic solid phase of the preferred composition was desired many of the components such as the paraffin, microcrystalline wax, petrolatum, beeswax, rapeseed oil, cocoa butter, castor oil, jojoba oil, dimethicone and essential oils were water insoluble while the other components such as the colorants, preservatives and iron oxides and titanium dioxides were in the form of heterogeneous wettable powders or soluble, it became necessary to employ a "two stage" bifluous method of emulsifying and thermo-mechanically intermixing the components to form a homogeneous evenly dispersed composition.

This is accomplished by employing two separate mechanical mixing devices whereby volume, temperature and flow can be controlled and varied dependently and respectively to achieve the desired flow and liquid viscosity and dispersal which are then proportionately fed volumetrically independently and separately bifluously into a thermo-mechanical high shear intermixer which blends together and emulsifies and intersperses interstitially the respective heterogeneous anhydrous hydrophobic insoluble and hydrophilic soluble components of the preferred composition into a respectively homogeneous liquid composition.

This is accomplished by heating and mechanically exciting and dispersing the solid wax components in one thermo-mechanical mixer until they become fluidized while simultaneous heating and exciting and dispersing the liquid components of the oils in a separate thermo-mechanical mixer into which the colorants, preservatives and fragrances are added. The out put and flow of these two separate thermo-mechanical mixers is then fed at different respective flow rates, temperatures, velocities and volumes bifluously into a common high shear mixer having a separate temperature, flow and volume which thixotropically blends and intersperses the heated heterogeneous fluids interstitially into a homogeneous fluid which is then expelled as a liquid into the hairstick container/dispenser where it is cooled and solidified.

The objective of this process is to evenly disperse, emulsify and intersperse the active soluble and insoluble ingredients throughout the composition with the heterogeneous hydrophobic insoluble components surrounding or encapsulating the soluble hydrophilic active components in an inverted emulsion in a homogeneous liquid phase followed by a cooling down into a homogeneous solid phase.

The container/dispensers/applicators are filled with the preferred composition in a hot liquid phase and as the liquid cools down it solidifies into the cylindrical container/dispenser which is then capped, labeled and prepared for shipment.

| PREFERRED COMPOSITIONS | | | |
|---|---|---|---|
| | Compositions (In Percent by Weight) | | |
| | 1 | 2 | 3 |
| Eskar Wax (Paraffin) | 20.4% | 18% | 15% |
| Microcrystalline Wax | 18 | 14 | 13 |
| Petrolatum | 15 | 23 | 26 |
| Beeswax | 8 | 12 | 13 |
| Rapeseed Oil | 7 | 4.5 | 6 |
| Coca Butter | 6 | 8 | 7.5 |
| Mica | 5 | 3 | 4 |
| Castor oil (PEG) | 4 | 2.6 | 3.6 |
| Jojoba Oil | 3 | 2 | 2.5 |
| Mineral Oil | 8.6 | 7 | 3.7 |
| Dimethicone CoPolyol | 1.5 | 2 | 1.7 |
| Fragrances | 1 | 1.3 | 1.5 |
| Methyl Paraben | .5 | .5 | .5 |
| Triclosan/Irgasan (C12H7CL3O2) | .4 | .5 | .4 |

-continued

PREFERRED COMPOSITIONS

| | Compositions (In Percent by Weight) | | |
|---|---|---|---|
| | 1 | 2 | 3 |
| Propyl Paraben | .1 | .1 | .1 |
| D & C Yellow #1 | | | |
| D & C Violet #2 | | | |
| D & C Red #17 | | | |
| D & C Green #6 | 1.5 | 1.5 | 1.5 |
| Iron Oxide | | | |
| Titaniaum Dioxide | | | |
| | 100 | 100 | 100 |

I have also discovered that there are synergistic benefits to including other trace additives to the solid wax-based carrier of the preferred embodiment. These are additives that when used, in combination, create desired adhesion, enhance or highlight color, inhibit microorganisms, strengthen the hair, impart gloss, sheen or shine to the hair: and, simultaneously add improved humectant properties while providing body and volume to the hair when used in combination with certain fragrant and desired hydroalcoholic aqueous extracts of flowering plants which have desirable olfactory aromatic sensations on subjects to which it is applied.

When used in a professional hair styling salon it becomes necessary to apply the preferred composition successively to more than a single subject's hair. Thus, contact with one subject can contaminate the preferred composition in the applicator container/dispenser apparatus with microorganisms sloughed off the subject's hair which adhere to the preferred composition which can be transmitted to a subsequent subject or client. To overcome this I have discovered that by inserting an impermeable membrane incrementally, evenly interspersed in the body of the preferred composition within the container dispenser/applicator apparatus an application can be made to a given subject or client and when the styling process is completed, the preferred composition is mechanically extruded out and the membranous septum manually peeled off with the contaminated layer just used and sanitarily discarded. This process exposes a new uncontaminated incremental layer for subsequent application to a new subject.

The process I discovered for producing the preferred composition and creating and inserting the impermeable membrane in the preferred composition is depicted in the attached drawings.

Layered Composition and Dispenser

To produce a container/dispenser/applicator apparatus filled with a layered composition separated by an interspersed impermeable membranous film, or foil separator, I have discovered that by further processing the homogeneous hot liquid phase of the preferred composition out of the thermo-mechanical intermixer into an extruder which has a variable slit, or slot, through which the preferred composition can be extruded and spread at desired thickness, temperature, width and flow rate volumetrically upon a suitable impermeable film, foil or membrane subsequently cooled to a solid state, then cut-to-size and stacked like a sandwich alternately into a desired thickness of alternating film and composition and then inserted into a press comprised of a set of dies into which the tubular container/dispensers are inserted and then subsequently pressed into the sandwiched laminate of alternate membranous foil or film and preferred composition thus filling the container/dispensers to a desired depth which act as the die cutting edge much like a cookie cutter (see diagram).

Afterward the filled containers are capped, labeled and prepared for shipping. The "flashing" residue of the sandwiched laminate consisting of alternate film and preferred composition with the oval holes cut out of it are then recycled by heating it, liquefying the preferred composition, which separates the dividing film from the preferred composition and the recovered preferred composition is deposited into container/dispensers without the separators or re-extruded into a new continuous film/foil separator for subsequent die cutting.

The product with the separators in the container/dispenser is principally desired for use and sale to professional hairstylists which would apply the product to different subjects and would be used to avoid cross-contamination or microorganisms between different subjects that a shared cosmetic would otherwise risk and otherwise avoid time consuming and expensive sanitizing practices before working on subsequent subjects or clients.

Figure 4:
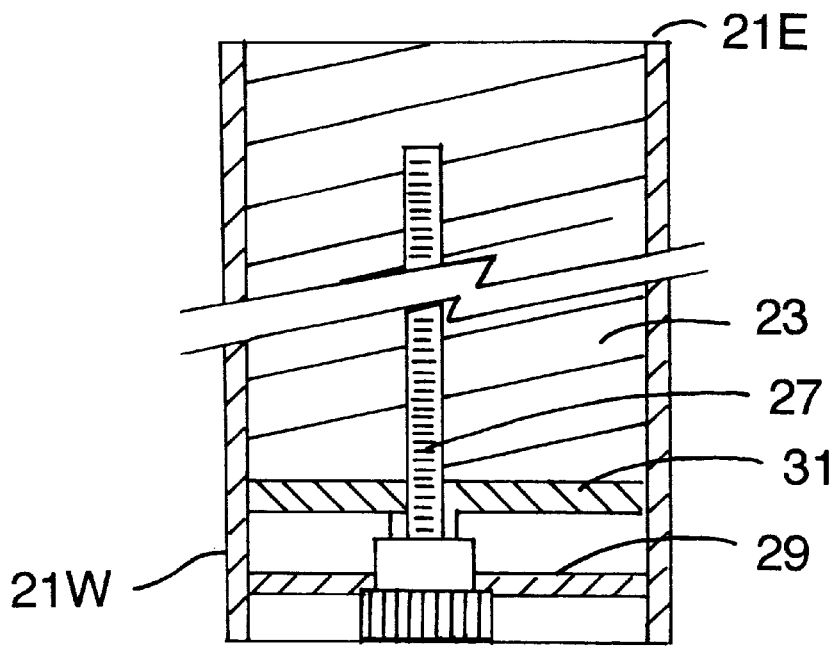
FIG. 4 is a partial cross-section of the hair styling stick of the invention.

Referring to the drawings, the hairstyling stick of the invention comprises an oval tubular shaped plastic container 21 having the composition 23 of the invention located therein. A wheel 25 is provided for moving the composition out of the container 21 for use. A removable cover 24 is provided to cover the composition when not in use. As shown in FIG. 4, the wheel has a threaded shaft 27 which is rotatably secured to a movable plate 29 fixed to the wall 21W of the container for pushing a movable plate 31 toward the open end 21E of the container for moving the composition 23 out of the container.

Figure 2:
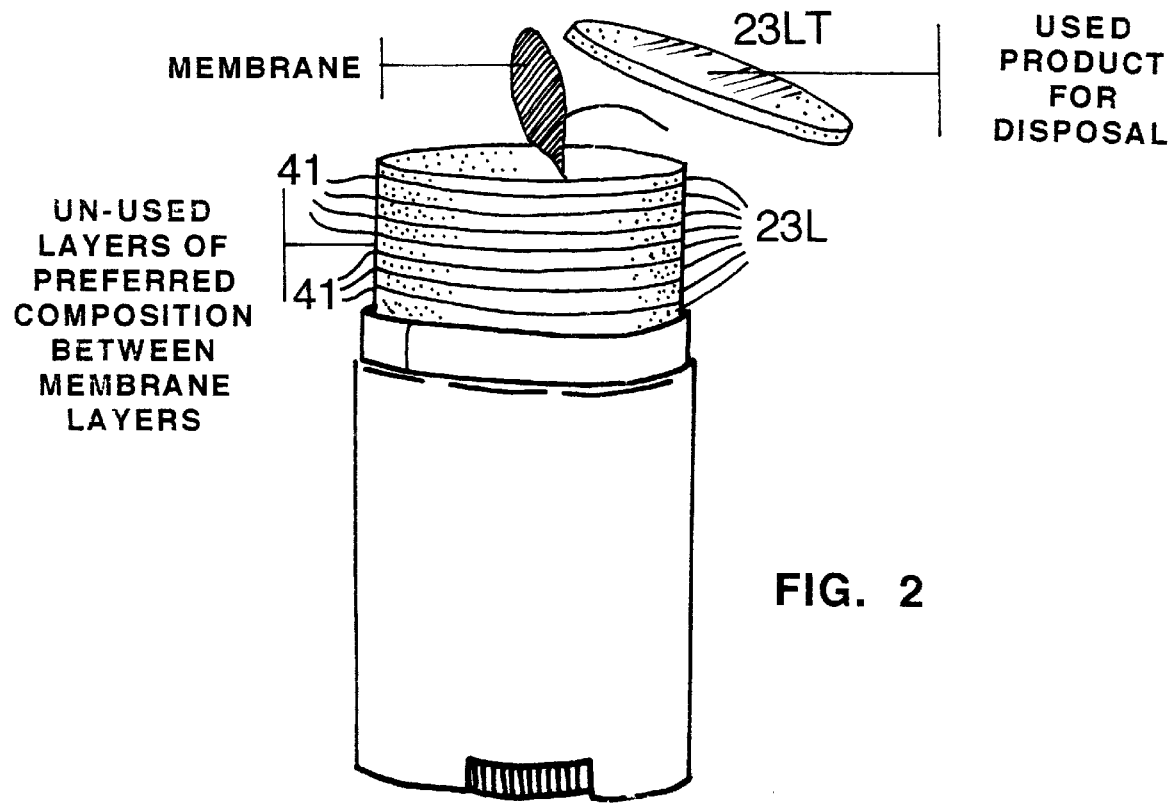
FIG. 2 illustrates the layers of the composition of the invention separated by membrane layers.
Figure 3:
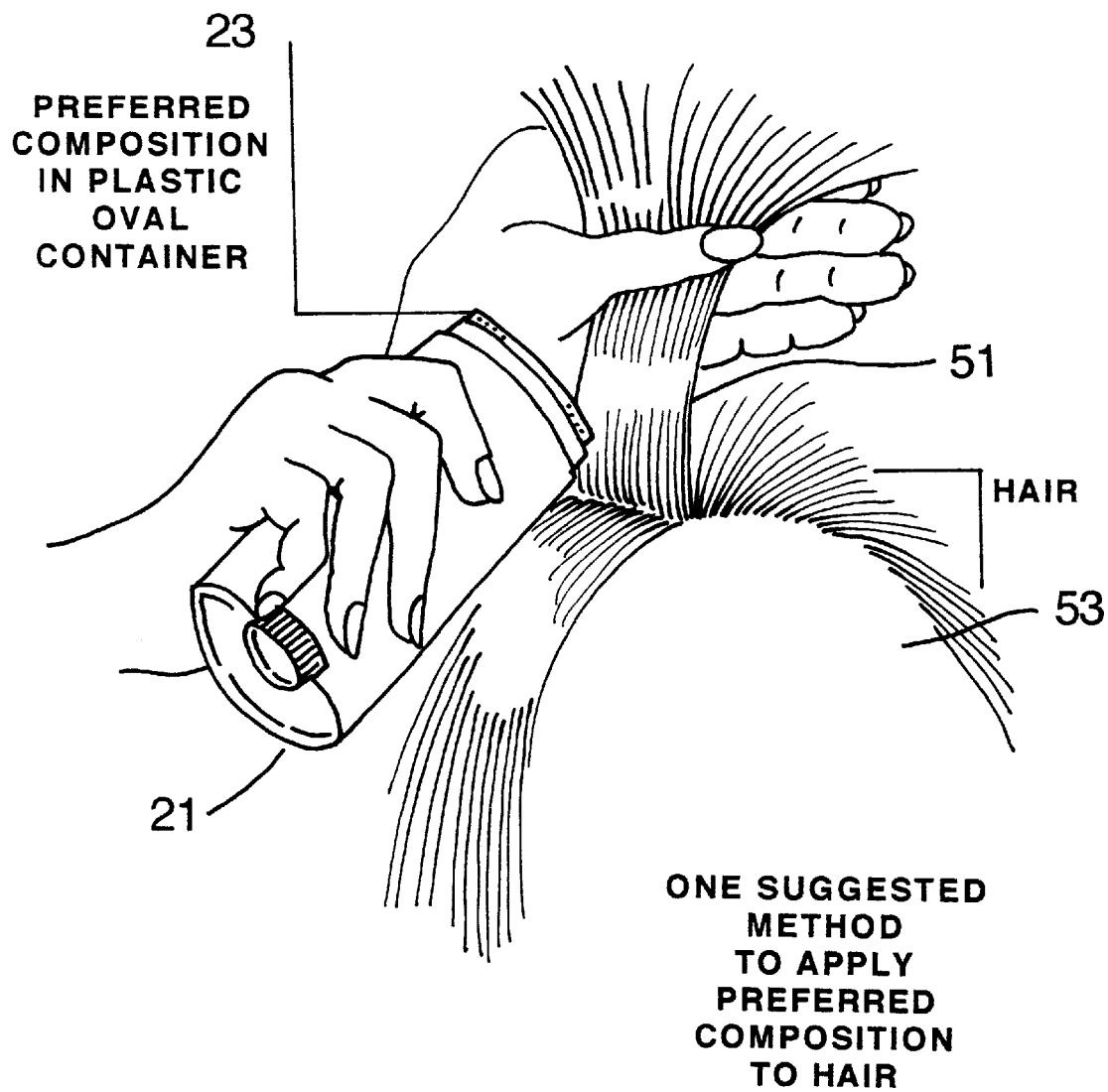
FIG. 3 illustrates one process of using the hairstyling stick of FIGS. 1 and 2.

Referring to FIG. 2, the composition 23 comprises separate layers 23L separated by thin foil membrane layers 41 such that the top used layer 23LT and the supporting membrane 41 may be removed to allow the next layer 23L to be used. This provides a sanitary arrangement whereby the operator of an establishment may use the hair styling stick on different customers. FIG. 3 illustrates the stick being used to apply the composition 23 to the hair 51 of a person 53 using one of the processes described previously.

Figure 5:
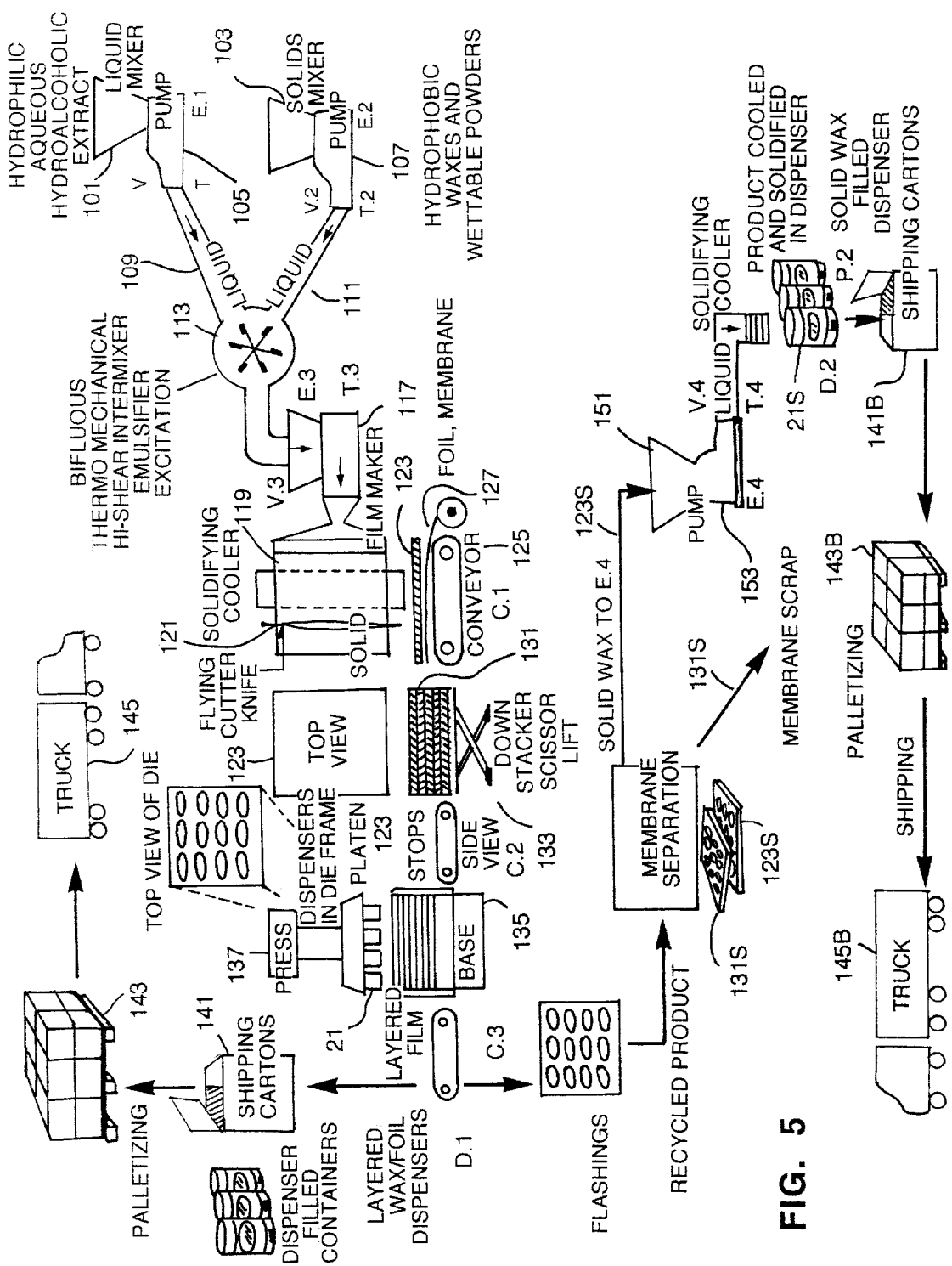
FIG. 5 illustrates the process for producing the hair styling stick of the invention.

Referring to FIG. 5, the process of making the stick with layers 23L separated by the removable membranes 41 will be described. Two mixers 101 and 103 are provided with mixer 101 being used to mix hydrophilic aqueous hydroalcohol extracts and mixer 103 being used to mix hydrophobic waxes and oils and wettable powder. The mixers are thermo-mechanical mixers which mix their components until they become fluidized. Extruder pumps 105 and 107 are provided for pumping the liquid through conduits 109 and 111 to a mixer 113 which is a thermo mechanical high-shear mixer for mixing the materials in conduits 109 and 111.

Figure 6:
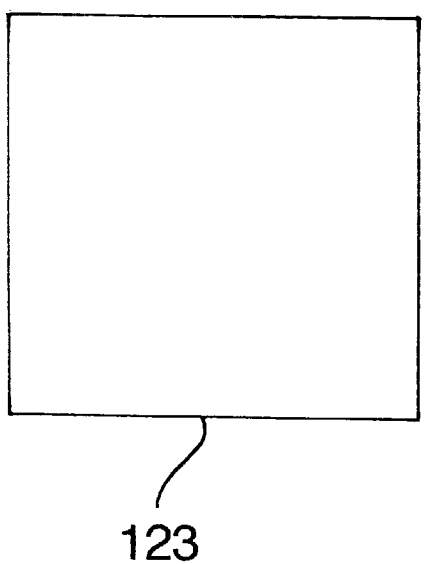
FIG. 6 is a top view of a stack of material slices and foil separating layers.
Figure 7:
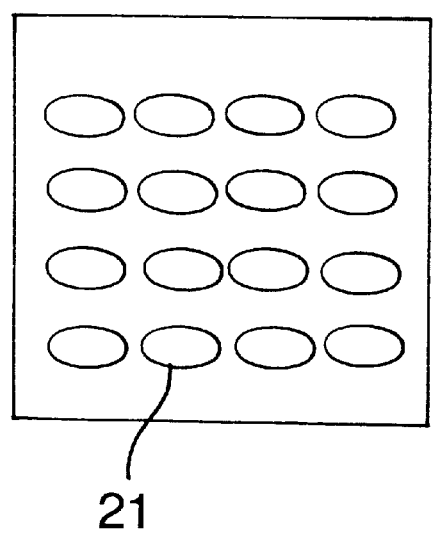
FIG. 7 is a bottom view of a press showing the open ends of containers held by the press.

The output of the mixer 113 is applied by way of conduit 115 to an extruder 117 which extrudes the mixed material into a solidifying cooler 119 which has a square interior. A cutter knife 121 cuts the material in square slices 123. A conveyor 125 conveys a thin strip 127. The slices fall onto the membrane strip 127. As the knife cuts the composition material into square slices 123, each slice falls onto the strip 127 and the knife 121 cuts this strip 127 such that a square slice 123 resting on a square foil membrane 131 is conveyed onto a down stacker scissor lift 133 such that square material slices 123 and foil separating layers 131 alternately are formed on the stacker 133 to form a stack of the slices 123, 131. A top view of the stack on the stacker 133 is shown in FIG. 6. Each stack is applied to a base 135 under a press 137 which supports a plurality of the empty containers 21 with their open end 21E facing downward. Note also FIG. 7. The containers 21 act as dies and as they are pressed onto the stack, they cut the layers such that the alternate layers 23L and 41 of composition and foil membranes are forced into the containers 21. The covers 24 are placed on the filled containers which are placed in shipping cartons 141A which are placed on pallets 143A and then loaded into trucks 145A. The left over or scrap layers 123S, 131S are separated from into composition layers 123S and membranes 131S and the composition material layers 123S are sent to a mixer 151 which forms a fluid mixture which is pumped by a pump 153 to empty containers 21S and the composition is cooled in the containers 21S. These containers 21S have only the composition with no alternate layers of membrane. The covers 24 are applied to the containers 21S which then are sold to individuals rather than to hair styling shops. The containers are placed in shipping cartons 141B which are placed on pallets 143B and then loaded into trucks 145B. The left over membrane layers 131S are disposed of.

What is claimed is:

1. A solid phase anhydrous hydrophobic antiseptic colored hair holding fixative adhesive hairstick composition of not more than 2% water of hydration in an invert emulsion, comprising:

a combination of hydrophobic solid waxes and liquid oils wherein said hydrophilic liquid oils are derived from organic vegetative and proteinaceous oils and inorganic and mineral oils and are emulsified with the co-polymers polyethelene glycol and dimethicone copolyol, the total of which in combination is not less than 90% by weight of said composition, a combination of fragrances, microbial biocides and methyl and propyl paraben in combination with the viricide $C_{12}H_7CL_3O_2$, the total concentration of which does not exceed 2% by weight of said composition, and colorants comprised of the combination of mica, iron oxide, titanium dioxide, D&C Yellow number 1, D&C violet number 2, D&C Red number 17, and D&C green number 6 which do not in combination exceed a total concentration of 7% by weight of said composition.

2. The composition of claim 1 wherein said liquid oils are comprised of natural and synthetically derived oil consisting of petrolatum, rapeseed oil, cocoa butter, castor oil, jojoba oil and mineral oil which in combination do not comprise less than 15% nor more than 35% by weight of said composition.

3. The composition of claim 1 wherein said hydrophobic solid waxes comprise paraffin, microcrystalline and beeswax which in combination comprises not less than a concentration of 35% nor more than 50% by weight of said composition.

4. A solid phase anhydrous hydrophobic antiseptic colored hair holding fixative adhesive hairstick composition of not more than 2% water of hydration in an invert emulsion comprising:

a combination of hydrophobic solid waxes and liquid oils wherein said hydrophilic liquid oils are derived from organic vegetative and proteinaceous oils and inorganic and mineral oils and are emulsified with the co-polymers polyethelene glycol and dimethicone copolyol, the total of which in combination is not less than 90% by weight of said composition, a combination of fragrances, microbial biocides and methyl and propyl paraben in combination with the viricide $C_{12}H_7CL_3O_2$, the total concentration of which does not exceed 2% by weight of said composition, and colorants comprised of the combination of mica, iron oxide, titanium dioxide D&C Yellow number 1 D&C violet number 2, D&C Red number 17, and D&C green number 6 which do not in combination exceed a total concentration of 7% by weight of said composition, wherein said combination of methyl and propyl parabens and $C_{12}H_7CL_3O_2$ are effective at concentrations of not more than 2% by weight of said composition in controlling, inhibiting or destroying certain molds, yeasts, fungi, gram negative and gram positive bacteria and certain viruses.

5. The composition of claim 1 in which the fragrances, colorants and microbial biocides do not comprise less than 5% nor more than 9% by weight of said composition.

6. The composition of claim 1 wherein the hairstick composition is located in an oval shaped tubular sleeve with an open end and an opposite end with means to mechanically extrude incrementally in a graduated manner, said composition out of said open end of the tubular sleeve.

7. A solid phase anhydrous hydrophobic antiseptic colored hair holding fixative adhesive hairstick composition of not more than 2% water of hydration in an invert emulsion, comprising:

a combination of hydrophobic solid waxes and liquid oils wherein said hydrophilic liquid oils are derived from organic vegetative and proteinaceous oils and inorganic and mineral oils and are emulsified with the co-polymers polyethelene glycol and dimethicone copolyol, the total of which in combination is not less than 90% by weight of said composition, a combination of fragrances, microbial biocides and methyl and propyl paraben in combination with the viricide $C_{12}H_7CL_3O_2$, the total concentration of which does not exceed 2% by weight of said composition, and colorants comprised of the combination of mica, iron oxide, titanium dioxide D&C Yellow number 1, D&C violet number 2, D&C Red number 17, and D&C green number 6 which do not in combination exceed a total concentration of 7% by weight of said composition, and not less than 80% nor more than 90% by weight of a combined blend of solid hydrophobic insoluble waxes derived from mineral, vegetative sources with not more than 20% nor less than 10% by weight of the total of trace additives comprised of polyethylene glycol, and colorants with a blend of aromatic fragrant extracts of vegetative plants, respectively.

* * * * *